United States Patent [19]
Bosworth et al.

[11] Patent Number: 5,078,986
[45] Date of Patent: Jan. 7, 1992

[54] METHOD FOR ENHANCING MAGNETIC RESONANCE IMAGING USING AN IMAGE ALTERING AGENT CONTAINING AN EXCESS OF CHELATING AGENT

[75] Inventors: Mark E. Bosworth, St. Louis; Ronald M. Hopkins, Chesterfield, both of Mo.

[73] Assignee: Mallinckrodt Medical, Inc., St. Louis, Mo.

[21] Appl. No.: 567,850

[22] Filed: Aug. 13, 1990

Related U.S. Application Data

[60] Continuation of Ser. No. 311,163, Feb. 15, 1989, which is a continuation of Ser. No. 114,159, Oct. 27, 1987, abandoned, which is a continuation of Ser. No. 832,356, Feb. 24, 1986, abandoned, which is a division of Ser. No. 476,565, Mar. 18, 1983, abandoned.

[51] Int. Cl.⁵ .................. A61K 31/20; A61K 31/195; G01N 31/00; G01N 24/00
[52] U.S. Cl. ............................ 424/9; 424/2; 436/173; 436/806; 514/558; 514/563; 514/974
[58] Field of Search ............... 424/9, 2; 436/173, 806; 128/653 AF, 654, 653 CA, 653 R; 514/558, 563, 974

[56] References Cited

U.S. PATENT DOCUMENTS

| | | | |
|---|---|---|---|
| 3,932,657 | 1/1976 | Rahman | 514/574 |
| 4,016,290 | 4/1977 | Rahman | 514/566 |
| 4,224,179 | 9/1980 | Schneider | 264/4.6 |
| 4,397,846 | 8/1983 | Weiner et al. | 514/104 |
| 4,497,791 | 2/1985 | Gamble et al. | 424/1.1 |
| 4,544,545 | 10/1985 | Ryan et al. | 424/1.1 |
| 4,647,447 | 3/1987 | Gries et al. | 424/9 |
| 4,863,717 | 10/1989 | Keana | 424/9 |

OTHER PUBLICATIONS

Hart, M., U.S.A.E.C. Orins-12, 118–135 (1956).
Caride, V. J., Relaxation Enhancement Using Liposomes Carrying Paramagnetic Species Magnetic Resonance Imaging, 2:107–112 (1984).

Primary Examiner—Glennon H. Hollrah
Assistant Examiner—Gary E. Hollinden
Attorney, Agent, or Firm—Senniger, Powers, Leavitt & Roedel

[57] ABSTRACT

Nuclear magnetic resonance (NMR) imaging of body organs and tissues is enhanced by administering to a living animal body a substantially nontoxic paramagnetic image altering agent comprised of a composition containing a chelate of a paramagnetic element, such as manganese, gadolinium or iron, carried by a liposome. The chelate is carried by or within the external surface of the liposome in such a manner that after arrival at or delivery to the desired organ or tissue site, the paramagnetic image altering agent is released in a diagnostically useful fashion.

19 Claims, No Drawings

5,078,986

METHOD FOR ENHANCING MAGNETIC RESONANCE IMAGING USING AN IMAGE ALTERING AGENT CONTAINING AN EXCESS OF CHELATING AGENT

This is a continuation, of application Ser. No. 07/311,163, filed Feb. 15, 1989, which is a continuation of application Ser. No. 07/114,159, filed Oct. 27, 1987 now abandoned which is a continuation of application Ser. No. 07/832,356, filed Feb. 24, 1986 now abandoned, which is a division of application Ser. No. 07/476,565, filed Mar. 18, 1983 now abandoned.

BACKGROUND OF THE INVENTION

This invention relates to nuclear magnetic resonance (NMR) imaging, and more particularly, to methods and compositions for enhancing NMR imaging.

The recently developed technique of NMR imaging encompasses the detection of certain atomic nuclei utilizing magnetic fields and radio-frequency radiation. It is similar in some respects to x-ray computed tomography (CT) in providing a cross-sectional display of the body organ anatomy with excellent resolution of soft tissue detail. As currently used, the images produced constitute a map of the distribution density of protons and/or their relaxation times in organs and tissues. The technique of NMR imaging is advantageously noninvasive as it avoids the use of ionizing radiation.

While the phenomenon of NMR was discovered in 1945, it is only relatively recently that it has found application as a means of mapping the internal structure of the body as a result of the original suggestion of Lauterbur (Nature, 242, 190–191, 1973). The fundamental lack of any known hazard associated with the level of the magnetic and radio-frequency fields that are employed renders it possible to make repeated scans on vulnerable individuals. Additionally, any scan plane can readily be selected including transverse, coronal and sagittal sections.

In an NMR experiment, the nuclei under study in a sample (e.g. protons) are irradiated with the appropriate radio-frequency (RF) energy in a highly uniform magnetic field. These nuclei as they relax subsequently emit RF at a sharp resonant frequency The coupling frequency (RF) of the nuclei depends on the applied magnetic field.

According to known principles, nuclei with appropriate spin when placed in an applied magnetic field (B, expressed generally in units of gauss or tesla ($10^4$ gauss)) align in the direction of the field. In the case of protons, these nuclei precess at a frequency $f=42.6$ B MHz at a field strength of 1 Tesla. At this frequency, an RF pulse of radiation will excite the nuclei and can be considered to tip the net magnetization out of the field direction, the extent of this rotation being determined by the pulse duration and energy. After the RF pulse, the nuclei "relax" or return to equilibrium with the magnetic field, emitting radiation at the resonant frequency. The decay of the signal is characterized by two relaxation times, i.e., $T_1$, the spin-lattice relaxation time or longitudinal relaxation time, that is, time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In NMR imaging, scanning planes and slice thickness can be selected. This permits high quality transverse, coronal and sagittal images to be obtained directly. The absence of any moving parts in NMR imaging equipment promotes a high reliability. It is believed that NMR imaging has a greater potential than CT for the selective examination of tissue characteristics in view of the fact that in CT, x-ray attenuation coefficients alone determine image contrast whereas at least four separate variables ($T_1$, $T_2$, proton density and flow) may contribute to the NMR signal. For example, it has been shown (Damadian, Science, 171, 1151, 1971) that the values of the $T_1$ and $T_2$ relaxation in tissues are generally longer by about a factor of 2 in excised specimens of neoplastic tissue compared with the host tissue.

By reason of its sensitivity to subtle physiochemical differences between organs and/or tissues, it is believed that NMR may be capable of differentiating different tissue types and in detecting diseases which induce physiochemical changes that may not be detected by x-ray or CT which are only sensitive to differences in the electron density of tissue. NMR images also enable the physician to detect structures smaller than those detectable by CT and thereby provide comparable or better spatial resolution.

As noted above, two of the principal imaging parameters are the relaxation times, $T_1$ and $T_2$. For protons (or other appropriate nuclei), these relaxation times are influenced by the proton's environment (e.g., viscosity, temperature).

These two relaxation phenomena are essentially mechanisms whereby the initially imparted radiofrequency energy is dissipated to the surrounding environment. The rate of this energy loss or relaxation can be influenced by certain other nuclei which are paramagnetic and chemical compounds incorporating these paramagnetic nuclei may substantially alter the $T_1$ and $T_2$ values for nearby protons. The extent of the paramagnetic effect of a given chemical compound is a function of the environment within which it finds itself.

As the use of NMR imaging grows in acceptance, there will be a corresponding increase in the need for enhancing NMR images and for favorably influencing $T_1$ and $T_2$ relaxation times through the use of agents which enhance NMR images.

SUMMARY OF THE INVENTION

Among the several objects of the invention may be noted the provision of methods for enhancing NMR imaging of body organs and tissues; the provision of such methods which utilize substantially nontoxic paramagnetic image altering agents which alter proton signals in their immediate vicinity; and the provision of methods of this type which advantageously shorten the scanning time for NMR imaging; and compositions for use in NMR imaging which provide improved organ specificity. Other objects and features will be in part apparent and in part pointed out hereinafter.

Briefly, the invention is directed to a method for enhancing NMR imaging of body organs and tissues which comprises administering a substantially nontoxic paramagnetic image altering agent to a living animal body in a sufficient amount to provide enhancement of NMR images of said body organs and tissues, the substantially nontoxic paramagnetic image altering agent containing a chelate of a paramagnetic element carried by a liposome.

DESCRIPTION OF THE PREFERRED EMBODIMENTS

In accordance with the present invention, it has now been found that NMR images of body organs and tissues may be usefully enhanced through the administration to a living animal body of a substantially nontoxic paramagnetic image altering agent prior to carrying out NMR imaging. The substantially nontoxic paramagnetic image altering agent may be a chelate of a paramagnetic element, e.g. manganese, gadolinium, cobalt, chromium, nickel and iron or other elements of the lanthanide series.

Paramagnetic elements such as manganese are capable of altering or enhancing NMR images, i.e. they are capable of altering the NMR signal characteristics of body tissues, organs or fluids and thus aid in differentiating normal from diseased tissue. Administered as free ionic salts (e.g. chlorides), they also exhibit some target organ specificity (e.g. liver, heart). However, such paramagnetic compounds undesirably exhibit significant toxicity.

Water-soluble chelates of paramagnetic elements are relatively or substantially nontoxic and are therefore useful for enhancing NMR images by favorably altering proton density or relaxation times or rates $T_1$ and $T_2$ and thereby affording improved contrast between normal and diseased tissues or organs. For this purpose, any of the conventional or common chelating agents may be used including, for example, ethylenediaminetetraacetic acid (EDTA) and salts thereof, diethylenetriamine pentaacetic acid (DTPA) and salts thereof, nitrilotriacetic acid (NTA) and salts thereof, trans-1,2-diaminocyclohexane-N,N,N',N'-tetraacetic acid and salts or hydrates thereof, 1,3-diamino-2-hydroxypropyl-N,N,N',N'-tetraacetic acid and salts or hydrates thereof and ethyleneglycol-bis (beta-aminoethyl ether)-N,N-tetraacetic acid. Thus, in the practice of the invention, various chelates of paramagnetic elements may be employed as a substantially nontoxic paramagnetic image altering agent, such as aqueous solutions containing disodium (ethylenediaminetetraacetato)manganese (II) with calcium disodium ethylenediaminetetraacetate as an additive and aqueous solutions of disodium (diethylenetriaminepentaacetato)gadolinium (III) with or without an additive such as calcium trisodium diethylenetriamine pentaacetate. These chelates should be administered at a pH of approximately 6.0-7.5.

As shown by the biodistribution studies set forth in detail hereinafter, a paramagnetic image altering agent such as a manganese chelate is not only substantially nontoxic but has also been found to accumulate or become generally distributed in body organs and tissues such as the liver, bone and marrow, muscle and kidneys and has the capability for enhancement of NMR images for hepatic and renal imaging.

Further, in order to improve the organ target specificity of such chelates while retaining the advantageous low toxicity thereof, it has been found desirable in accordance with the present invention to administer the paramagnetic image altering agent in a form in which the chelate of a paramagnetic element is carried to a desired site by means of a liposome. Such preparations are particularly suitable for enhancement of NMR images of the reticuloendothelial system (RES) since the liposome provides greater liver/spleen specificity by permitting the chelate to be present in such organs in greater concentrations and for longer residence periods than would otherwise be found with the chelate alone. The liposome functions as a carrier for delivering the paramagnetic image altering chelate to the desired organs without itself significantly altering the NMR proton signals. A typical preparation of this nature is disodium (ethylenediaminetetraacetato)manganese (II) contained in solution and within multilamellar liposomes as illustrated in greater detail hereinafter. The chelate is carried by or within or outside the external surface of the liposome in such a manner that after arrival at or delivery to the desired organ or tissue site, the paramagnetic image altering agent is released in a diagnostically useful fashion.

Liposomes generally comprise lipid materials including lecithin and sterols and the liposomes employed herein may contain egg phosphatidyl choline, egg phosphatidic acid, cholesterol and alpha-tocopherol in various molar ratios and the lipids may be present at various total concentrations. Useful liposomes may be prepared as generally described in Kimelberg et al., CRC Crit. Rev. Toxicol. 6 25 (1978), Papahadjopoulos, Ann. Reports in Med. Chem., 14 250-260 (1979) and Olson et al., Biochim. Biophys. Acta., 557 9-23 (1979). The preparation of liposomes and their release and stability characterics are also described in Yatvin et al., Medical Physics, Vol. 9, No. 2, 149 (1982).

The substantially nontoxic paramagnetic image altering agents are administered to a living animal body or mammalian species in a sufficient amount to provide enhancement of NMR images of body organs and tissues prior to obtaining an NMR scan or scans of such organs and tissues with "slices" being taken at the level of the desired organ at various time periods post-administration.

The following examples illustrate the practice of the invention.

Example 1

The following paramagnetic image altering agents or compositions were prepared.

(A) An aqueous solution containing 4.6% disodium (ethylenediaminetetraacetato)manganese (II) with 1% calcium disodium ethylenediaminetetraacetate, pH 6.9.

(B) An aqueous solution containing 4.6% disodium (ethylenediaminetetraacetato)manganese (II) with 0.67% calcium disodium ethylenediaminetetraacetate, pH 6.9.

(C) Aqueous 10% and 20%, w/v, solutions of disodium (diethylenetriaminepentaacetato)gadolinium (III), pH 6.8.

(D) Aqueous (10.14%, w/v) solution of disodium (diethylenetriaminepentaacetato)gadolinium (III) with 1.30% calcium trisodium diethylenetriamine pentaacetate.

(E) Aqueous solution (5.66%, w/v) of disodium (trans-1,2-diaminocyclohexane-N,N,N',N'-tetraacetate) manganese dihydrate.

Example 2

A liposome preparation of disodium (ethylenediaminetetraacetato)manganese (II) (EDTA) (composition A in Example 1) for use in NMR imaging was prepared according to the following procedure.

Egg phosphatidyl choline (396 mg) (PC) (type V-E, Sigma Chemical Co.), dipalmitoyl phosphatidic acid (85.6 mg) (PA)(Sigma), cholesterol (153.4 mg) (CH)(Sigma), and alpha-tocopherol (14.14 mg) (a-T)(Sigma) were combined in a 150 ml glass round-bottom flask. This was done by dispensing appropriate volumes of stock solutions of these compounds (chloroform-methanol solutions stored at −15° C.). Total solvent volume in the flask was 75.8 ml at this point. An additional 50 ml chloroform was added, and then the flask was placed on a rotary evaporating unit (Buchi, Type KRvr) utilizing dry iceacetone in the condenser. A water bath (approx. 45° C.) was placed under the flask, in contact with the lower third of the flask. The solvents were then dried off as the evaporator vacuum was raised gradually. The lipids were dried to a thin, even film covering approximately one half of the flask area. This process required approximately 15 minutes. The flask was then removed from the evaporator and connected directly to the laboratory vacuum. The purpose of this step was to ensure removal of residual organic solvents. This vacuum step was done for approximately 1 hour at room temperature. For this preparation, the flask was then taken off the vacuum, stoppered, then placed at −15° C. overnight. On the following day, the flask was placed on the laboratory vacuum at room temperature for 1 hour. Then 55 ml of composition A of Example 1 was dispensed into the flask and the flask was stoppered. The flask was then swirled by hand so that the solution was swept across the dried lipid. The lipid gradually became suspended in the solution, and the end point was that at which all the lipid had been visually dispersed from the wall of the flask. This required 45 minutes for this preparation. At this point, the liposomes had been formed (Kimelberg et al., "Properties and Biological Effects of Liposomes and their Uses in Pharmacology and Toxicology", CRC Crit. Rev. Toxicol. 6 25 (1978) and Papahadjopoulos, "Liposomes as Drug Carriers", Ann. Reports in Med. Chem., 14 250-260 (1979)). For this preparation, the liposome lipid composition was egg PC/PA/CH/a-T=8/2/6/.5, expressed on a molar ratio basis, and the total lipid concentration was 20 micromoles/ml. The liposomes were then transferred to a glass beaker and then aspirated into a 25 ml glass syringe with a luer fitting. A 25 mm Swinnex filter housing (Millipore Corp.) was then connected to the syringe. The housing had previously been fitted with a 25 mm 1.0 micron pore size Unipore membrane with a polyester post filter (both from Bio-Rad Corp.). The liposomes were then extruded through the membrane by depressing the syringe plunger. This process was repeated until all 55 ml were extruded. This step was done to narrow the liposome size distribution (Olson et al., "Preparation of Liposomes of Defined Size Distribution by Extrusion through Polycarbonate Membranes", Biochem. Biophys. Acta., 557 9-23 (1979)). There is no retention of lipid by the membrane and so the liposome lipid concentration remains the same. The sizing effect is presumably done by breaking the larger liposomes down to smaller ones as they pass through the membrane pores. Fifty ml of the liposomes were then placed in a 50 ml glass vial with an 890 gray stopper. The vial was placed in a refrigerated container for use in NMR imaging.

Example 3

A liposome preparation of manganous disodium ethylenediaminetetraacetate (composition B in Example 1) for use in NMR imaging was prepared according to the following procedure.

Egg phosphatidylcholine (769 mg), egg phosphatidic acid (172 mg)(Avanti Polar Lipids, Inc.), cholesterol (446.5 mg), and alpha-tocopherol (27.55 mg) were combined in a 250 ml round-bottom flask. Solvent volume at this point was 179 ml. The solvents were then dried, and the lipids deposited on the flask walls, in the same manner as for the Example 2 batch. The dried lipids were placed on the laboratory vacuum as before, and then immediately afterward, 48 ml of composition B of Example 1 were added to the flask, and the lipid was dispersed as described previously in Example 2. The dispersal process required 1.5 hours to complete, and 10-15 small glass beads (2 mm diameter) were used during the last 5 minutes to help disperse the lipid. For this preparation, the liposome lipid composition was egg PC/egg PA/CH/a-T=8/2/9/.5, and the lipid concentration was 50 micromoles/ml. The liposomes were then extruded, in the same manner as before, through a 1.0 micron pore size Unipore membrane. Thirty minutes prior to this, several 6-inch lengths of dialysis tubing (Spectrapor, 1 inch width, 10,000 MW, Spectrum Medical Industries, Inc.) were placed in 0.9% NaCl to hydrate. After extrusion, the liposomes were transferred to these bags (5 required) and the bags were clamped off. Approximately 0.5 ml of liposomes were held aside. The bags were placed in a 4 L beaker containing 3.8 L of 0.9% NaCl, pH 6.4. The bags float because of the plastic dialysis bag clamps used. A magnetic stirring bar was placed in the beaker, and the beaker was covered with aluminum foil and placed on a magnetic stirrer (Thermodyne Inc., Type Nuova II) in a 5° C. cold room. The stirrer was turned up to the point at which the bags were gently agitated. After 18 hours, the bags were placed in a beaker of fresh, precooled 0.9% NaCl, and the dialysis was continued. After 23.5 hours, the beaker was removed from the cold room, the bags were cut open, and the liposomes were transferred to a previously cooled 50 ml glass vial and stoppered. The vial was placed in a refrigerated container for use in NMR imaging. The purpose of this dialysis step was to remove the non-liposome-entrapped Mn-EDTA from the preparation. The Mn-EDTA concentration in the entrapped aqueous solution remained the same as it was before dialysis, but the external (i.e. non-liposome-entrapped) aqueous solution now consisted of just 0.9% NaCl.

Example 4

Acute intravenous toxicity testing was performed in mice with manganese(II) chloride ($MnCl_2$), composition B of Example 1 (containing 4.6% manganous disodium ethylenediaminetetraacetate with 0.67% calcium disodium ethylenediaminetetraacetate), the composition of Example 2 and a concentrated aqueous suspension of the negatively charged liposomes alone in phosphate-buffered saline, test substances 1 through 4, respectively. In addition, the cardiotoxic effects of single bolus intracoronary arterial injections of 4, 8, 16 or 32 mg $MnCl_2$ were evaluated in the isolated perfused rabbit heart (IPRH).

The manganese(II) chloride was dissolved in sterile water for injection, USP (SWFI; Abbott Laboratories) to yield unhydrated salt concentrations of 0.25%, w/v and 0.8% w/v for the mouse and IPRH testing, respectively. The aqueous vehicle for the suspension of negatively charged liposomes consisted of 0.9% NaCl buffered with 0.003M sodium phosphate, pH 7.4. The lipid concentration was 50 μmol/ml.

A total of 60 mice, 30 males (body weight range of 20-33.5 g) and 30 females (body weight range of 19.1-29.7 g) were used. Fifty of the mice were Swiss ICR, CD-1, obtained from Charles River and ten were Swiss CF-1 obtained from Sasco (Omaha, Nebr.).

A total of 8 female, New Zealand albino rabbits, with body weights ranging from 1.97-2.96 kg were used in the study. Data from only six rabbit heart experiments are presented because the first two were used as preliminary range-finding experiments.

Acute Intravenous Toxicity in Mice

The four test substances were administered via the lateral tail vein of the mouse at a rate of 1 ml/min with the following doses given.

| Test Sub- stance | Dose (mg/kg) | Cumulative 7-Day Mortalities/ Number Dosed | | Average Change in Body Wt. (g) of Survivors | | $LD_{50}$ (mg/kg) |
|---|---|---|---|---|---|---|
| | | Male | Female | Male | Female | |
| 1 | 25 | 3/5 | 1/5 | 1.2 | 2.7 | 28.0 |
| | 31.25 | 2/5 | 4/5 | 4.6 | 3.5 | |
| | 37.5 | 4/5 | 4/5 | 3.4 | 3.6 | |
| 2 | 460 | 0/1 | 0/1 | 0.1 | 0.7 | >2300 |
| | 920 | 0/1 | 0/1 | 2.8 | 3.6 | |
| | 1840 | 0/3 | 0/3 | 3.0 | 1.7 | |
| | 2300 | 0/2 | 0/2 | 0.8 | 0.1 | |
| 3 | 2300 | 0/2 | 0/2 | 0.4 | 0.4 | >2300 |
| 4 | 625* | 0/2 | 0/2 | 5.0 | 4.0 | >2500* |
| | 1250* | 0/2 | 0/2 | 5.1 | 4.7 | |
| | 2500* | 0/2 | 0/2 | 5.5 | 3.7 | |

*μ mol lipid/kg

| Test Sub- stance | Concentration of Test Substance (% w/v) | Dose Level (mg/kg) | Dose Volume (ml/kg) | Number of Mice Injected | |
|---|---|---|---|---|---|
| | | | | Male | Female |
| 1 | 0.25 | 25 | 10 | 5 | 5 |
| | 0.3125 | 31.25 | 12.5 | 5 | 5 |
| | 0.375 | 37.5 | 15 | 5 | 5 |
| 2 | 4.6 | 460 | 10 | 1 | 1 |
| | | 920 | 20 | 1 | 1 |
| | | 1840 | 40 | 3 | 3 |
| | | 2300 | 50 | 2 | 2 |
| 3 | 4.6 (20μ mol lipid/ml) | 2300 | 50 | 2 | 2 |
| 4 | 50μ mol lipid/ml | 625* | 12.5 | 2 | 2 |
| | | 1250* | 25 | 2 | 2 |
| | | 2500* | 50 | 2 | 2 |

*μ mol lipid/kg

Following injections, mice were observed for immediate reactions and then daily throughout a 7-day observation period, at which time survivors were killed and body weights determined. The method of Litchfield and Wilcoxon (J. Pharmacol. Exp. Ther. 96:99-113, 1949) was used to calculate the $LD_{50}$ for $MnCl_2$ (test substance 1).

Intracoronary Cardiotoxicity in the Isolated Perfused Rabbit Heart (IPRH)

Rabbits were sacrificed by cervical dislocation, the hearts excised and coronary perfusion was performed at constant pressure via the aortic root using an oxygenated physiological salt solution (Chenoweth's solution) heated to 37° C. A 0.8%, w/v, solution of $MnCl_2$ was heated to 37° C. and intracoronary bolus injections of 0.5, 1.0, 2.0 and 4.0 ml were made in each of the six hearts via a sidearm of the perfusion apparatus. A period of time sufficient to allow the heart to stabilize was allowed between injections. The heart rate (HR), contractile force (CF) and electrocardiogram (ECG) were recorded on a Grass Model 7 polygraph. The maximal percentage changes from pre-injection control values for HR and CF were determined during intervals of 0.15 and 15-30 seconds after injection. The percentage changes from control HR and CF were also recorded at 1, 2, 3 and 4 minutes after injection. The ECG was examined for arrhythmias. When ventricular fibrillation (VF) occurred, no calculations were performed with CF and HR data from that injection.

RESULTS

Acute Intravenous Toxicity in the Mouse

Lethality and body weight data are summarized in the following table:

Transient convulsions, of moderate severity, were noted in each animal receiving $MnCl_2$. With the exception of one, all deaths were observed within one minute after dosing was completed. The apparent cause of death was cardiac arrest as ascertained by thoracotomy of one mouse just after cessation of respiration. The one delayed death was 4 days after dosing but that animal had shown no prior signs of toxicity other than the convulsions observed immediately after dosing. The $MnCl_2$ $LD_{50}$ of 28 mg/kg corresponds to 0.22 mmol/kg of Mn(II). The $LD_{50}$ Mn(II) may be compared to the intravenous does of 0.05 mmol/kg which was used in dogs to enhance NMR images of myocardial infarcts (Brady et al., Radiology 144:343-347, 1982).

Neither test substance 2 ($MnNa_2$ EDTA) nor test substance 3 ($MnNa_2$ EDTA/liposome formulation) caused death at doses up to 2300 mg/kg of $MnNa_2$ EDTA. Larger doses were not given because dose volumes would have been excessive. However, the 2300 mg/kg dose of $MnNa_2$ EDTA did appear to impair weight gain as evidenced by data for both test substances 2 and 3. There were also slight increases or decreases in motor activity in a majority of mice receiving test substances 2 and 3 at all dose levels. The 2300 mg/kg dose, which is obviously considerably lower than the $LD_{50}$, corresponds to 6.03 mmol/kg of Mn(II).

Disodium (ethylenediaminetetraacetato)manganese (II) (test substance 2) had a much lower degree of acute intravenous toxicity than $MnCl_2$. There were no deaths at a dose of test substance 2 which was 27 times as great as the $LD_{50}$ dose of $MnCl_2$ when compared on the basis of manganous content. The acute toxicity of disodium (ethylenediaminetetraacetato)manganese (II) did not appear to be changed by partial incorporation (5%, v/v, entrapped) into negatively charged liposomes (test substance 3). A concentrated suspension of liposomes alone failed to elicit any toxic effects following intravenous administration to mice (test substance 4).

Test substance 4, a phosphate buffered saline suspension of liposomes with 50 μmol lipid/ml, was nontoxic in doses up to 50 ml/kg, a dose considered to be the maximal safe dose volume. No adverse reactions were observed and body weight gain was normal. Test substance 4 contained 2.5 times the lipid content of test substance 3 in an attempt to increase the likelihood that liposome-induced toxicity might be manifested.

Coronary Cardiotoxicity of $MnCl_2$ (test substance 1) in the IPRH

The results are summarized as follows:

| Dose of $MnCl_2$ (mg) | Means % Change in Contractile Force (CF) at Times after Dosing | | | | Mean % Change in Heart Rate (HR) at Times after Dosing | | | | Incidence of Ventricular Fibrillation (VF) |
|---|---|---|---|---|---|---|---|---|---|
| | 0–15 S | 15–30 S | 1M | 2M | 0–15 S | 15–30 S | 1M | 2M | |
| 4 | −5 | −28 | −12 | +5 | −2 | −2 | −4 | −2 | 0/6 |
| 8 | −74 | −38 | −17 | +2 | −8 | −7 | −7 | −6 | 0/6 |
| 16 | −92 | −61 | −37 | −1 | −31 | −14 | −14 | −11 | 2/6 |
| 32 | −100* | −64 | −33 | +2 | −100* | −17 | −17 | −14 | 5/6 |

*Represents value from only 1 heart, all others had VF. This heart demonstrated complete atrio-ventricular (A-V) block with ventricular standstill.

Dose-related decreases in CF and HR were observed. Those effects were maximal within the period of 0–15 seconds after injection and the parameters either returned to control levels or stabilized at a new baseline within two minutes after injection.

A dose-related incidence of arrhythmias was also observed. The VF reported in the above table did revert spontaneously to normal sinus rhythm in each instance but one (a 32 mg dose). However, VF would not be expected to revert spontaneously under clinical conditions. The single heart at the 32 mg dose of $MnCl_2$ which failed to fibrillate did have a period of complete A-V conduction block with ventricular standstill. At the 16 mg dose, two of the four hearts which did not fibrillate had premature ventricular contractions during or immediately after injection. No arrhythmias were observed at the lower two doses.

In addition to the arrhythmias described above, examination of ECG tracings revealed dose-related increases in PR and QRS intervals indicative of conduction delays.

Intravenous $MnCl_2$ displayed a high degree of acute toxicity in mice with convulsions the primary pharmacotoxic sign and cardiac arrest the probable cause of death.

In the isolated perfused rabbit heart, $MnCl_2$ caused dose-related depression of contractility and heart rate and caused conduction delays and ventricular arrhythmias. The observed cardiac effects are consistent with the effects of calcium deprivation and probably relate to competition between manganous ion and calcium ion for physiological processes requiring calcium ion.

EXAMPLE 5

A study was carried out to compare the biodistribution of disodium (ethylenediaminetetraacetato)manganese (II) ($^{54}MnNa_2EDTA$) and a partially liposome-entrapped manganous disodium (ethyelendiaminetetraacetato) manganese (II) formulation ($^{54}Mn$-L).

Disodium (ethylenediaminetetraacetato)manganese (II) was supplied as a 5.2% w/v solution, at pH 6.8, containing 0.67% excess calcium disodium ethylenediaminetetraacetic acid and $^{54}MnCl_2$ (0.22 mCi/ml, ICN Pharmaceutical, Inc.) was added to the 5.2% w/v $MnNa_2$ EDTA solution to yield a final 4.6% w/v $^{54}MnNa_2EDTA$ solution with a radioactivity concentration of 12.5μCi/ml; the $^{54}MnNa_2EDTA$ was characterized by paper chromatography employing a 70% methanol/10% ammonium hydroxide (85:10) solvent system. 98.5% of the $^{54}Mn$ was recovered in a chromatographic peak corresponding to the Rf of $MnNa_2EDTA$.

$^{54}Mn$-L was prepared as described in Example 2 using an aliquot of the 4.6% w/v $^{54}MnNa_2EDTA$ solution. The percent liposomal entrapment for the $^{54}Mn$-L solution used in the study was 2.8%, w/v.

A total of forty Sprague-Dawley rats (20 male, 217–295 g; 20 female, 151–208 g; Charles River) were used. Drinking water was provided ad libitum. The animals, 2 males and 2 females per group, were selected randomly from their cages and were identified with indelible ink numbers at tail bases before test substance administration.

Rats were divided into 10 groups consisting of 2 male and 2 female rats per group. Five groups of rats received bolus intravenous injections of 2 ml/kg of 4.6% w/v $^{54}MnNa_2EDTA$ (25 Ci/kg) via a lateral tail vein. The remaining five groups received bolus 2 ml/kg intravenous injections of $^{54}Mn$-L (4.6% w/v $^{54}MnNa_2EDTA$; 2.8%, v/v, liposomal entrapment; 25 Ci/kg). Immediately after dosing, rats were housed in individual metabolism cages. Ground Purina Laboratory Chow and water were supplied ad libitum to animals sacrificed at 24 and 48 hr after treatment. Rats from both $^{54}NmNa_2EDTA$ and $^{54}Mn$-L treatment groups were sacrificed by cervical dislocation at 0.5, 2, 4, 24 and 48 hr after treatment, and the following samples were obtained: injection site, blood, liver, lung, spleen, heart, kidneys, salivary gland (submaxillary), brain, bone with marrow, muscle and fat. Urine samples were obtained from animals sacrificed at all intervals of 2 hr or more after injection and fecal samples were obtained from animals sacrificed at 24 and 48 hr after treatment. The following tissues were assumed to have the indicated percents of body weight: blood (8%), bone and marrow (11%), skeletal muscle (45.5%), and fat (7.1%). The entire organ weights were determined for the remaining tissues.

Levels of radioactivity in the biological specimens and aliquots of the injected test substances were determined using a gamma scintillation spectrometer (Model 1085, Nuclear Chicago Corp., Des Plaines, Ill.). Results were calculated on a percent dose/organ (or fluid) and a percent dose/g (or ml) basis using an HP-85 desk top computer (Hewlett Packard, Fort Collins, Colo.). Statistical comparisons between $^{54}MnNa_2EDTA$ and $^{54}Mn$-L treatment groups were performed using Student's t-test on each tissue, fluid or excreta at each time interval.

Kinetic data for the elimination of radioactivity from liver, spleen, kidneys, heart and bone with marrow were curve fitted by the peeling and least-square methods, to mono or bi-exponential equations:

$$Ct = \sum_{i=1}^{2} Aie - Kit$$

Where
Ct = % dose/organ in tissue at time t.
Ai = Concentration at time 0 of the line described by each first order term.
Ki = Elimination rate constant for each first-order term.

The half-life (t ½) for each elimination phase was calculated as 0.693/Ki. The square of the correlation coefficient ($r^2$) for each elimination phase was calculated as an indication of variability.

RESULTS $^{54}$MnNa$_2$EDTA was rapidly cleared from blood following intravenous administration. Thirty minutes after dosing, 2.1% of the total radioactivity remained in the blood and within 2 hr less than 0.1% remained in the blood. A similar blood disappearance was observed following intravenous administration of $^{54}$MnNa$_2$EDTA and $^{54}$Mn-L at any time interval.

On a percent dose/organ basis, $^{54}$MnNa$_2$EDTA distributed primarily to the liver, bone with marrow, muscle and kidneys. Unusually high levels of radioactivity were observed in fat samples obtained from 2 of 4 rats sacrificed at 0.5, 2 and 4 hr after dosing resulting in a large standard error at these points. $^{54}$Mn-L exhibited a similar distribution pattern as $^{54}$MnNa$_2$EDTA. However, significantly higher % dose/organ values for $^{54}$Mn-L were observed in the spleen at each time interval, in the liver at 4 and 24 hr after dosing and in the heart at 2 hr after dosing. Additionally, the percent dose accumulated in fat was consistently less for $^{54}$Mn-L compared to $^{54}$MnNa$_2$EDTA, although a significant difference in fat radioactivity content was observed only at 48 hr after injection.

Hepatic and renal clearances of $^{54}$MnNa$_2$EDTA and $^{54}$Mn-L were biphasic consisting of an initial rapid elimination (t ½ < 1 hr) followed by a secondary slow elimination phase (t ½ > 17 hr). Approximately 92% of the hepatic $^{54}$MnNa$_2$EDTA and 86% of the hepatic $^{54}$Mn-L was associated with the rapid first phase hepatic elimination. Approximately 81% of the renal $^{54}$MnNa$_2$EDTA and 84% of $^{54}$Mn-L was associated with the rapid first phase renal elimination. $^{54}$MnNa$_2$EDTA was cleared from the spleen according to a monophasic elimination with a respective half-life of ~2 hr. $^{54}$Mn-L, on the other hand, underwent biphasic splenic elimination. Approximately 5% of the splenic $^{54}$Mn-L was eliminated in the first phase with a half-life of ~2 hr, whereas the remaining radioactivity was slowly eliminated from the spleen with a half life of ~13 hr. Both test substances were cleared from the heart according to a monophasic elimination with half-lives of approximately 8 hr. Clearance of radioactivity from the bone and marrow was relatively slow following intravenous administration of both test substances as indicated by half-lives > 100 hr.

Highest tissue concentrations were observed in the liver and kidneys following intravenous administration of $^{54}$MnNa$_2$EDTA. Liver/blood and kidney/blood ratios for $^{54}$MnNa$_2$EDTA were 11.3 and 9.1, respectively, 30 minutes after treatment. By 2 hr after treatment, $^{54}$MnNa$_2$EDTA was almost completely cleared from the blood and tissue/blood ratios greater than 10 were observed for liver, kidney, salivary gland, bone and marrow, heart and fat, although fat tissue concentrations were extremely variable. A similar tissue concentration profile was obtained for $^{54}$Mn-L with the major exception that significantly higher splenic concentrations were observed at each time interval after $^{54}$Mn-L administration. The spleen/blood ratio for $^{54}$Mn-L was 45.6 at 2 hr after treatment compared to a spleen/blood ratio of 6.8 for $^{54}$MnNa$_2$EDTA at the same time interval.

$^{54}$MnNa$_2$EDTA and $^{54}$Mn-L exhibited similar biphasic excretory profiles. Initially after administration of test substance, radioactivity was rapidly excreted in the urine resulting in >50% of the dose being eliminated within 2 hr after treatment. At later time intervals, no additional urinary excretion of radioactivity was observed. The remaining radioactivity was primarily eliminated via the feces. Within 48 hr after treatment, 31 and 24% of the total doses of $^{54}$MnNa$_2$EDTA and $^{54}$Mn-L had been excreted in the feces, respectively. The remaining radioactivity in the rats after 48 hr was primarily localized in the bone and marrow.

In summary $^{54}$MnNa$_2$EDTA and $^{54}$Mn-L were rapidly cleared from the blood following intravenous administration. Similar biodistribution profiles were obtained from both compositions with the major exception of significantly higher splenic tissue concentrations at each time interval after administration of $^{54}$Mn-L.

Example 6

A study was carried out to compare the biodistribution of the following test substances (each prepared at pH 6.7 was approximately radioactivity concentrations of 12.5 μCi/ml):

Test Substance

1 - $^{54}$Mn-disodium (ethylenediaminetetraacetato)-manganese (II), 4.6% w/v, solution containing 0.66%, w/v, excess calcium disodium ethylenediaminetetraacetate.

2 - $^{54}$Mn-disodium (ethylenediaminetetraacetato)-manganese (II), 23.0%, w/v, solution containing 3.30%, w/v, excess calcium disodium ethylenediaminetetraacetate.

3 - A negatively charged liposome formulation containing encapsulated $^{54}$MnNa$_2$EDTA. The liposomes consisted of phosphatidylcholine, phosphatidic acid, cholesterol and μ-tocopherol (8/2/9/.5) and were dispersed in Test substance 1 (12.5 μCi/ml). Liposomes were dialyzed against normal saline prior to injection in order to remove unencapsulated $^{54}$MnNa$_2$EDTA Greater than 98.5% of the radioactivity was entrapped following dialysis. The liposome entrapment of Test substance 1 was 9.0%, v/v, and the lipid concentration was approximately 50 μmol/ml.

4 - A positively charged liposome formulation containing encapsulated $^{54}$MnNa$_2$EDTA. The liposomes consisted of phosphatidyl choline, stearylamine, cholesterol and α-tocopherol (8/2/9/.5) and were dispersed in Test substance 1 (12.5 μCi/ml). Liposomes were dialyzed against normal saline prior to injection in order to remove unencapsulated $^{54}$MnNa$_2$EDTA. Greater than 98.5% of the remaining radioactivity was entrapped following dialysis. The liposome entrapment of Test substance 1 was 12.8%, v/v, and lipid concentration was approximately 50 μmol/ml.

A total of 80 Sprague Dawley rats (40 male, 168-212 g, 40 female, 149-180 g) were used. Drinking water was provided ad libitum. Rats were individually marked with indelible ink numbers at the tail base for identification prior to test substance identification.

The rats of each of four treatment groups (each group consisting of 10 males and 10 females) received single 2 ml/kg intravenous injections of each of the four test substances. Animals were sacrificed at 0.5, 2, 4, 24 and 48 hours after treatment and an extensive number of tissues were sampled for radioactivity determination. In addition, urine samples were obtained from rats sacrificed at time intervals >0.5 hour and fecal samples at 24 and 48 hours after treatment. Urine samples collected from rats treated with test substances 1 and 2, sacrificed at 48 hours were analyzed by paper chromatography for the presence of radioactive metabolites. The unencapsulated solutions (test substances 1 and 2) accumulated on a dose-dependent, apparently saturable, basis primarily in liver, small intestine, bone and marrow, muscle and kidney. The liposome entrapped solutions (test substances 3 and 4) accumulated in extremely high concentrations in the liver and spleen indicating uptake by the reticuloendothelial system. In addition, relatively high concentrations of all four formulations tested were observed in glandular organs such as the pancreas and salivary gland. The unencapsulated formulations (test substances 1 and 2) tended to undergo faster tissue elimination than the entrapped formulations (test substances 3 and 4).

Test substances 1 and 2 were eliminated from the liver, kidney and spleen via biphasic kinetics indicating heterogeneous cellular compartmentalization of the $^{54}MnNa_2EDTA$. Test substances 3 and 4 were eliminated from most organs slowly via monophasic kinetics indicating homogenous cellular distribution. In addition, the negatively charged liposome formulation (test substance 3) was more rapidly cleared from the liver and radioactivity accumulated faster in the small intestine compared to test substance 4.

Test substances 1 and 2 were excreted primarily via the urine with urinary excretion complete within 2 hours after treatment. Paper chromatography of urine collected from rats treated with test substances 1 and 2 suggested that $^{54}MnNa_2EDTA$ was excreted in the urine in unchanged form. At later times, test substances 1 and 2 were eliminated via the feces. Test substances 3 and 4 were excreted primarily via the feces and underwent very little urinary excretion (5%). The biological retention time of test substances 3 and 4 was prolonged compared to test substances 1 and 2.

In summary, test substances 3 and 4 were readily taken up by the reticuloendothelial system, were cleared from most organs at a slower rate than test substances 1 and 2 and were excreted primarily via the feces and undergo very limited urinary excretion whereas test substances 1 and 2 are excreted primarily via the urine.

Example 7

The acute intravenous toxicity of disodium (diethylenetriaminepentaacetato)gadolinium (III) (composition C of Example 1) was studied.

A total of 16 Swiss CF-1 albino mice (8 male, 22.0-25.6 g; 8 female, 18.2-24.1 g) were used. Picric acid markings were used for individual identification.

The protocol of Example 4 was used. Groups of 2-4 mice, with sexes equally represented, received single intravenous doses of the test substance according to the following schedule:

| $GdNa_2DTPA$ Solution Concentration (%, w/v) | Dose Volume (ml/10 g) | Intravenous Dose | | Number and Sex of Mice | |
|---|---|---|---|---|---|
| | | g/kg | mmol Gd/kg | Male | Female |
| 10 | 0.1 | 1.0 | 1.7 | 1 | 1 |
| 10 | 0.2 | 2.0 | 3.4 | 1 | 1 |
| 10 | 0.2 | 2.0 | 3.4 | 1 | 1 |
| 10 | 0.6 | 6.0 | 10.3 | 1 | 1 |
| 20 | 0.2 | 4.0 | 6.9 | 1 | 1 |
| 20 | 0.4 | 8.0 | 13.7 | 1 | 1 |
| 20 | 0.6 | 12.0 | 12.6 | 1 | 1 |

RESULTS

No deaths were observed following intravenous administration of $GdNa_2 DTPA$ at doses up to 12 g/kg. At doses $\geq$ g/kg, slight ataxia was observed immediately after dosing. Following administration of dose volumes of 0.6 ml/10 g, respiratory distress was observed. All mice appeared normal within 6 hours after treatment. A slight reduction in body weight, as summarized below, was observed in several mice the week following intravenous administration of $GdNa_2 DTPA$.

| Intravenous Dose (g/kg) | Mean Body Weight Change (g) | |
|---|---|---|
| | Male | Female |
| 1.0 | 2.3 | 0.7 |
| 2.0 | 2.0 | -0.8 |
| 4.0 | 2.6 | 1.3 |
| 6.0 | 2.8 | 1.4 |
| 8.0 | -1.3 | -0.2 |
| 12.0 | -1.4 | -1.4 |

The test substance ($GdNa_2 DTPA$) exhibited a relatively safe mouse acute intravenous toxicity profile as evidenced by the fact that no deaths were observed following intravenous administration of $GdNa_2 DTPA$ at doses up to 12.0 g/kg (20.6 mmol Gd/kg). The relatively low toxicity of $GdNa_2 DTPA$ suggests a high degree of chelate stability. These data indicate that $GdNa_2 DTPA$ is a relatively safe paramagnetic chelate.

Example 8

The preparation of Example 2 with manganous disodium ethylenediaminetetraacetate contained in solution within and outside multiamellar liposomes was administered to an anesthetized dog. The total dose was 25 ml of the preparation, 12 ml of which was administered by bolus injection and the remaining 13 ml by infusion over a 3-5 minute period. The dog was positioned on his back in a General Electric NMR clinical scanner. The desired level for transverse scanning was determined prior to the administration of the NMR enhancing preparation.

A first experiment involved a "slice" taken at the level of the kidneys in the dog. For this purpose, the first scan was obtained prior to administration of the preparation. Three additional scans were obtained at times corresponding to a) during the infusion, b) 35 minutes post-administration, and c) 75 minutes post-administration. In all three of these latter scans, good contrast was seen, with the extend of contrast dropping as the time increased. Not only were the kidneys visualized but surrounding fatty tissue and tissue from other areas were more readily contrasted. The experiment showed that the paramagnetic chelate preparation altered proton signals.

Subsequently, a pre-scan was taken at the level of the dog's liver and a comparable dose was then administered as before. Slices were taken at 12, 25 and 40 minutes post-administration. In all three of the latter scans, good contrast was seen, particularly of the liver and spleen.

EXAMPLE 9

Rabbits were anesthetized and surgically prepared for recording of arterial blood pressure. The EKG was recorded with surface electrodes. A preparation of composition D of Example 1 was administered intravenously, at doses of 0.1, 0.3 and 1.0 ml/kg (0.017, 0.034 and 0.17 mmol Gd(III)/kg), to groups of five rabbits at each dose level. Proton $T_1$ and $T_2$ values were determined on blood samples drawn before administration of the contrast agent and at time intervals of 5, 10 and 15 minutes after dosing, using a 0.12 T NMR spectrometer with a probe frequency of 5.1 mHz. Fifteen minutes after contrast injection, the rabbits were sacrificed and various tissues were removed for $T_1$ and $T_2$ determinations in the NMR spectrometer.

Cardiovascular effects were minimal. Dose-related changes in tissue and blood $T_1$ and $T_2$ values were observed. Changes in $T_1$ values were generally greater than changes in $T_2$ values. The most profound effects on $T_1$ were in blood and kidneys (both cortex and medulla) with large intestine, pancreas and stomach and the next most sensitive. The $T_1$ data obtained in comparison with normal $T_1$ values are presented in the following table:

| TISSUE | NORMAL TISSUE $T_1$ (msec) | MEAN TISSUE $T_1$ VALUES (msec) 15 MINUTES AFTER ADMINISTRATION OF THE DISODIUM (DIETHYLENE-TRIAMINEPENTAACETATO) GADOLINIUM (III) | | |
|---|---|---|---|---|
| | | 0.17 mmol/kg | 0.51 mmol/kg | 1.7 mmol/kg |
| Heart | 280 | 274 | 267 | 199 |
| Lung | 311 | 311 | 303 | 225 |
| Skel. Muscle | 215 | 215 | 217 | 173 |
| Liver | 171 | 169 | 172 | 145 |
| Spleen | 260 | 254 | 257 | 225 |
| Pancreas | 175 | 154 | 172 | 129 |
| Stomach | 245 | 245 | 219 | 159 |
| Small Intestine | 225 | 221 | 224 | 177 |
| Large Intestine | 220 | 215 | 228 | 143 |
| Renal Cortex | 374 | 194 | 137 | 72 |
| Renal Medulla | 252 | 200 | 130 | 47 |
| Fat | 57 | 63 | 61 | 64 |
| Blood | — | | | |
| Pre-contrast | — | 528 | 580 | 573 |
| 5 minutes | — | 413 | 292 | 135 |
| 10 minutes | — | 416 | 321 | 156 |
| 15 minutes | — | 421 | 337 | 169 |

EXAMPLE 10

Selective catheterization of the left anterior descending coronary artery or circumflex coronary artery was achieved via a percutaneous intracarotid artery approach in anesthetized dogs. Gelfoam plugs were inserted into the coronary artery, via the catheter, in order to produce coronary occlusion. Animals were treated with lidocaine to prevent coronary arrhythmias and morphine to relieve pain.

Twenty-four hours after coronary occlusion, four dogs received intravenous injections of 1 mg/kg (0.17 mmol Gd(III)/kg) of the preparation of composition D of Example 1 (GdNa$_2$DTPA). Dogs were sacrificed 10 minutes after dosing and proton $T_1$ values for normal and infarcted myocardial tissue were obtained using the -.12 T NMR spectrometer with a probe frequency of 5.1 mHz. $T_1$ values for myocardial tissue which had been normally perfused were reduced to 180 msec as compared to average myocardial $T_1$ values of 330 for untreated dogs. Infarcted regions of heart muscle had $T_1$ values of 290.

Two dogs received 2 ml/kg (0.34 mmol Gd(III)/kg) of the (GdNa$_2$DTPA) solution 24 hours after coronary artery occlusion. Blood samples were withdrawn before contrast administration and again 5 minutes and 10 minutes after dosing. Ten minutes after dosing the dogs were killed, the hearts removed intact and placed in the General Electric NMR scanner. Images of the excised hearts revealed marked differences between normal and infarcted tissues with the difference greater than that observed in hearts from dogs with infarcts who had not received a contrast enhancement agent. Blood remaining in the ventricles had a much different $T_1$ image after treatment with the contrast agent.

The blood samples and sections of the imaged hearts from the dogs receiving 2 ml/kg (0.34 mmol Gd(III)/kg) of the (GdNa$_2$DTPA) solution were assayed for proton $T_1$ values in the 0.12 T NMR spectrometer at a probe frequency of 5.1 mHz. Blood $T_1$ values dropped from an average of 510 msec before contrast administration to 50 and 100 msec at 5 minutes and 10 minutes after dosing. The normally perfused myocardium had an average $T_1$ values of 135 msec, as compared to untreated dog $T_1$ of 330, while infarcted tissue $T_1$'s averaged 230.

EXAMPLE 11

Two rabbits were anesthetized and abdominal NMR images were obtained in the General Electric NMR scanner. Rabbits then received intravenous doses of 0.3 ml/kg (0.5 mmol Gd(III)/kg) of the preparation of composition D of Example 1 (GdNa$_2$DTPA) and additional abdominal NMR images were made over a period of two hours after dosing. Marked alteration of renal medulla and renal cortex proton images were observed after administration of the GdNa$_2$DTPA with peak effects observed within 15 minutes.

EXAMPLE 12

Marmosets (5) were anesthetized and surgically prepared for recording of arterial blood pressure. The EKG was recorded with surface electrodes. A preparation of composition E of Example 1 was administered intravenously at a dose of 0.3 ml/kg (0.118 mmol Mn(II)/kg). Proton $T_1$ and $T_2$ values were determined on blood samples drawn before administration of the contrast agent and at time intervals of 5, 10 15 minutes after dosing, using a 0.12 T NMR spectrometer with a probe frequency of 5.1 mHz. Fifteen minutes after contrast injection, the monkeys were sacrificed and various tissues were removed for $T_1$ and $T_2$ determinations in the NMR spectrometer.

Cardiovascular effects were minimal. Blood (5 min) and liver $T_1$ values were substantially reduced and several other tissue $T_1$'a appeared to be slightly reduced (see following table):

| TISSUE | NORMAL $T_1$ | MONKEY (MARMOSET) TISSUE $T_1$ VALUES (MEAN) 15 MIN AFTER 0.3 ml/kg (0.118 mmol Mn (II)/kg) OF EXAMPLE 1 (E) |
| --- | --- | --- |
| Heart | 256 | 183 |
| Lung | 231 | 280 |
| Skeletal Muscle | 243 | 206 |
| Liver | 118 | 32 |
| Spleen | 245 | 221 |
| Pancreas | 313 | 103 |
| Stomach | 206 | 145 |
| Small Intestine | 199 | 107 |
| Large Intestine | 274 | 185 |
| Renal Cortex | 227 | 152 |
| Renal Medulla | — | 209 |
| Bladder | 261 | 217 |
| Fat | 67 | 68 |
| Blood | — | — |
| pre-contrast | | 507 |
| 5 minute | | 375 |
| 10 minute | | 454 |
| 15 minute | | 511 |

EXAMPLE 13

A rabbit received 10 ml/kg (approximately 0.1 mmol Mn(II)/kg) of a preparation with disodium (ethylenediaminetetraacetato)manganese (II) contained in solution within multilamellar liposomes (MnNa$_2$EDTA liposomes, test substance 3 of example 6). The rabbit was then anesthetized, placed in the General Electric NMR scanner and images of the abdominal area, including liver and spleen, were obtained over a period of 2–5 hours after dosing. Liver and spleen images were altered as compared to similar scans in untreated rabbits, while no effect was observed in intestine, kidney and skeletal muscle. The peak alterations of liver and spleen proton signals were observed at the beginning of the imaging period (two hours after dosing with the liposomal formulation).

EXAMPLE 14

Groups of two rabbits each received intravenous doses of 3 ml/kg or 10 ml/kg (approximately 0.03 or 0.1 mmol Mn(II)/kg) of a preparation with disodium (ethylenediaminetetraacetato)manganese (II) contained in solution within multilamellar liposomes (MnNa$_2$EDTA liposomes, test substance 3 of example 6) and were sacrificed at intervals of 2–14 hours after dosing. Liver and spleen proton $T_1$ values ere determined using a 0.12 T NMR spectrometer with a probe frequency of 5.1 mHz. Dose-related decreases in liver and spleen $T_1$ values were observed with peak effects at two hours (see following table):

| DOSE | TISSUE | NORMAL TISSUE $T_1$ (msec) | MEAN TISSUE $T_1$ VALUES (msec) AT VARIOUS TIMES AFTER ADMINISTRATION OF MnNa$_2$EDTA LIPOSOMES | | |
| --- | --- | --- | --- | --- | --- |
| | | | 2 hrs | 4 hrs | 12–14 hrs |
| 3 ml/kg | spleen | 260 | 99 | 133 | — |
| | liver | 171 | 99 | 131 | — |
| 10 ml/kg | spleen | 260 | 35 | 45 | 80 |
| | liver | 171 | 93 | 110 | 120 |

EXAMPLE 15

The plasma fragility of test substances 3 and 4 of example 6 was tested as follows: 0.5 ml each of liposomes and fresh dog plasma were mixed, then placed at 37° C. for 30 minutes. The mixture was then cooled and an aliquot was then run on a Sephadex G-50 column to separate the unentrapped (released) material from the liposome entrapped material. In both cases approximately 10–15% leakage had occurred, indicating that the liposomes were stable enough to use for in vivo imaging.

In view of the above it will be seen that the several objects of the invention are achieved and other advantageous results attains.

As various changes could be made in the above products and methods without departing from the scope of the invention, it is intended that all matter contained in the above description shall be interpreted as illustrative and not in a limiting sense.

What is claimed is:

1. A method for enhancing NMR imaging of body organs and tissues which comprises administering a diagnostically effective amount of a substantially non-toxic paramagnetic image altering agent to a living animal body in a sufficient amount to provide enhancement of NMR images of said body organs and tissues, said paramagnetic image altering agent containing a chelate of a paramagnetic element and an excess of a chelating agent as a salt of said chelating agent.

2. A method as set forth in claim 1 wherein said paramagnetic image altering agent is carried by a liposome.

3. A method as set forth in claim 1 or claim 2 wherein said paramagnetic element is selected from the group consisting of manganese, gadolinium, cobalt, chromium, nickel, iron, and other elements of the lanthanide series.

4. A method as set forth in claim 1 or claim 2 wherein said chelating agent is selected from the group consisting of ethylenediaminetetraacetic acid, diethylenetriamine pentaacetic acid, nitriloacetic acid, trans-1,2-diaminocyclohexane-N,N,N',N'-tetraacetic acid, 1,3-diamino-2-hydroxypropyl-N,N,N',N'-tetraacetic acid and ethyleneglycolbis (beta-aminoethyl ether)-N,N-tetraacetic acid.

5. A method as set forth in claim 1 or claim 2 wherein said salt of said chelating agent is selected from the group consisting of sodium, calcium, and mixtures thereof.

6. A method as set forth in claim 1 or clam 2 wherein said paramagnetic image altering agent contains manganous disodium ethylenediaminetetraacetate and calcium disodium ethylenediaminetetraacetate.

7. A method as set forth in claim 1 or claim 2 wherein said paramagnetic image altering agent contains gadolinium disodium diethylenetriamine pentaacetate and calcium disodium diethylenetriamine pentaacetate.

8. A method as set forth in claim 1 or claim 2 wherein said paramagnetic image altering agent contains gadolinium disodium diethylenetriamine pentaacetate and calcium trisodium diethylenetriamine pentaacetate.

9. A method as set forth in claim 1 or claim 2 wherein NMR images of the liver are enhanced.

10. A method as set forth in claim 1 or claim 2 wherein NMR images of the spleen are enhanced.

11. A method as set forth in claim 1 or claim 2 wherein NMR images of the heart are enhanced.

12. A method as set forth in claim 1 or claim 2 wherein NMR images of the glandular organs are enhanced.

13. A method as set forth in claim 1 or claim 2 wherein NMR images of the lung and lymphatic system are enhanced.

14. A method as set forth in claim 1 wherein said paramagnetic element is gadolinium.

15. A method as set forth in claim 1 wherein said paramagnetic element is manganese.

16. A method as set forth in claim 1 wherein said paramagnetic element is iron.

17. A method as set forth in claim 1 wherein said chelate of a paramagnetic element is a diethylenetriamine pentaacetic acid chelate of gadolinium.

18. A method as set forth in claim 17 wherein said salt of said chelating agent is a salt of diethylenetriamine pentaacetic acid.

19. A method as set forth in claim 1 wherein said salt of said chelating agent is a calcium salt.

* * * * *

UNITED STATES PATENT AND TRADEMARK OFFICE
CERTIFICATE OF CORRECTION

PATENT NO. : 5,078,986
DATED : January 7, 1992
INVENTOR(S) : Mark E. Bosworth It is certified that error appears in the above-identified patent and that said Letters Patent is hereby corrected as shown below:

On the title page, item [75] Inventors: please change to read as follows:

--Mark E. Bosworth, St. Louis, Mo. --.

Signed and Sealed this

Fourth Day of May, 1993

Attest:

MICHAEL K. KIRK

*Attesting Officer*   *Acting Commissioner of Patents and Trademarks*